United States Patent [19]

Felder et al.

[11] 4,044,048

[45] Aug. 23, 1977

[54] RADIOPAQUE ESTERS OF TETRA-IODOTEREPHTHALIC ACID

[75] Inventors: Ernst Felder, Riva S. Vitale, Switzerland; Davide Pitre, Milan, Italy

[73] Assignee: Bracco Industria Chimica Societa per Azioni, Milan, Italy

[21] Appl. No.: 684,724

[22] Filed: May 10, 1976

[30] Foreign Application Priority Data

June 16, 1975 Switzerland .......................... 7799/75

[51] Int. Cl.$^2$ ............................................. C07C 69/82
[52] U.S. Cl. ................................... 260/475 P; 424/5
[58] Field of Search ....................................... 260/475 P

[56] References Cited

PUBLICATIONS

Beelstein, Handbuch der Organischen Chemie, Sys. 978 Vierte Auflage, Band 9, p. 851, (1926).

*Primary Examiner*—Jane S. Myers
*Attorney, Agent, or Firm*—Hans Berman

[57] ABSTRACT

Compounds of the formula

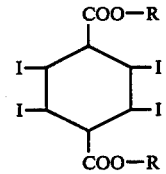

wherein R is $(C_mH_{2m}O_n)$—OH, $m$ being 2, 3, or 4, and $n$ being 0 or 1, are effective and well tolerated as X-ray contrast agents in lymphography, hepatography, bronchography, cystography, and hysterosalpingography.

11 Claims, No Drawings

RADIOPAQUE ESTERS OF TETRA-IODOTEREPHTHALIC ACID

This invention relates to X-ray contrast agents high in iodine content, and particularly to esters of tetra-iodoterephalic acid which are well tolerated.

The di-lower alkyl esters of tetra-iodoterephthalic acid have been known for a long time (Lutjens, Ber. O. chem. Ges. 29 2837), but are so slowly released from the human body after injection into body cavities as to cause side reactions.

It has now been found that esters of the formula

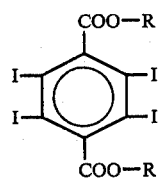

wherein R is $(C_mH_{2m}O_n)$—OH, m being 2, 3, or 4, and n being 0 or 1, are excreted from the human body fast enough to make them useful as X-ray contrast agents. The rate of excretion is controlled by the chemical nature of the alcohol moities in the esters. Under otherwise analogous conditions, two available hydroxyl groups in each alcohol moiety cause faster excretion than a single hydroxyl group.

The compounds of the invention are useful in lymphography, particularly lymphadenography, and the most quickly excreted compounds of the invention are used to advantage in hepatography. When suitably compounded, the esters of the invention are used successfully in bronchography, cystography, and hysterosalpingography, but also for visualizing the gastrointestinal tract.

As compared to the only contrast agent practically available heretofore for lymphadenography, the mixed ethyl esters of the iodized fatty acids of poppy seed oil, the esters of the invention have the advantage of a strong chemical bond between iodine and the benzene ring which prevents the formation of significant amounts of iodine ions in the body.

As compared to the esters of tetra-iodo-o-phthalic acid, the esters of the invention have the advantage of being hydrolyzed to the well tolerated tetra-iodoterephthalic acid, whereas tetra-iodo-o-phthalic acid is poisonous. The respective $LD_{50}$ values determined in mice after intravenous injection of 50% solutions are 5600 mg/kg and 380 mg/kg. The esters of the invention are even better tolerated than the free acid. Their $LD_{50}$ values are generally higher than 10 g/kg body weight in mice.

For lymphadenography, the esters of the invention are micronized prior to injection of their suspensions into a lymphatic vessel, accumulate in the lymph nodes, and are excreted after gradual dissolution of the crystals in lymph or after metabolic decomposition.

In contact with compounds of radioactive iodine, the esters of the invention become radioactive by exchange of iodine atoms, and may thus be employed for scintigraphy. Radioactive esters of the invention are also obtained by synthesis from tetra-iodoterephthalic acid or its derivatives containing radioactive isotopes of iodine.

The esters of the invention are prepared in a basically conventional manner. For lymphography, they are administered preferably in the form of suspensions of their micronized crystals in isotonic, aqueous sodium chloride solution (normal saline solution) containing 150 – 500 mg iodine per milliliter. For bronchography and hysterosalpingography, carboxymethylcellulose or other pharmaceutically acceptable thickeners are added to the suspension to achieve a desired viscosity.

METABOLISM

A suspension of bis-2-hydroxyethyl tetra-iodoterephthalate in physiological salt solution containing 200 mg iodine per ml was injected into the tail veins of rats at a dosage of 1 g iodine per kg body weight, and the amount of iodine in the urine and feces discharged by the test animals was determined by means of an autoanalyzer. Within seven days after application, 18% of the injected iodine was excreted with the urine and 23% with the feces. Thin layer chromatography of the excreted material indicated that the bis-2-hydroxyethyl ester of tetra-iodoterephthalic acid was partly discharged without chemical change, partly hydrolyzed to the corresponding mono-ester, and partly to the free acid.

When the same suspension was injected intraperitoneally, the same metabolites were found in the urine. The mono-ester predominated. The iodine content of the urine discharged within 8 days amounted to 8.52%, and within 13 days it amounted to 9.66% of the total amount injected. The bis-2,3-dihydroxypropyl ester of tetra-iodoterephthalic acid and its metabolites were excreted even more rapidly. 3.15% Iodine, based on the amount injected i.p. as above, was excreted with the urine within 24 hours.

When a corresponding suspension of the known dimethyl tetra-iodoterephthalate was injected intraperitoneally, the total amount of iodine excreted with the urine in 8 days amounted to only 0.018% of the injected amount.

LYMPHOGRAPHY

Aqueous suspensions of bis-2-hydroxyethyl tetra-iodoterephthalate, bis-2,3-dihydroxypropyl tetra-iodoterephthalate, and dimethyl tetra-iodoterephthalate were injected into superficial lymph vessels of six dogs each between a paw and the corresponding knee. Each suspension contained 200 mg iodine per ml, and 4 ml suspension was administered to each dog over a period of 30 minutes. Radiographs were made daily for one month, and less frequently thereafter.

The 2-hydroxyethyl and methyl esters were somewhat superior to the 2,3-dihydroxypropyl ester in the contrast of the X-ray images obtained, but none of the images was less than good. The same properties were observed as to penetration of the contrast agents through the first lymph node and visualization of the associated ducts and nodes.

The 2-hydroxyethyl ester was cleared from the lymph vessels in 24 days and from the nodes in 9 days. The 2,3-dihydroxypropyl ester could no longer be detected in the lymph vessels after 33 days and in the lymph nodes after 5 days. When the last tests were made 226 days after administration, the lymph vessels and nodes of the dogs injected with the dimethyl ester were still carrying the contrast agent.

INDIRECT LYMPHOGRAPHY

When suspensions of the crystalline esters of the invention were injected intraperitoneally in test animals, the lymph vessels and lymph nodes below the sternum could be visualized in radiographs without difficulty. In some instances even the retroperitoneal lymph system could be visualized. This was not possible heretofore with the known iodized oils which remain at the point of injection.

The following Examples illustrate the preparation of the radiopaque compounds of the invention.

EXAMPLE 1

21.4 g Di-sodium tetra-iodoterephthalate (0.03 mole) and 0.5 g sodium iodide were stirred in 35 ml ethylene chlorohydrin for 20 hours at 100° C. The reaction mixture was cooled to ambient temperature and stirred into 350 ml water. The bis-2-hydroxyethyl ester of tetra-iodoterephthalic acid was precipitated in crystalline form, recovered, and washed with sodium carbonate solution and water. The dried crystals weighed 21.1 g (97% yield). When recrystallized from methanol, they melted with decomposition at 264° C. A thin layer chromatogram with ethyl acetate/isopropanol/aqueous ammonia 11:7:4 gave an $R_f$ value of 0.88. The ester was identified by elementary analysis:

Calculated for $C_{12}H_{10}I_4O_6$: 19.02% C; 66.99% I. Found: 19.18% C; 67.26% I.

EXAMPLE 2

19.4 g Di-sodium tetra-iodoterephthalate (0.0272 mole) and 0.5 g sodium iodide were stirred in 35 ml 3-chloro-1,2-propanediol for 20 hours at 100° C, the reaction mixture was worked up as in Example 1, and the bis-2,3-dihydroxypropyl ester of tetra-iodoterephthalic acid was obtained in an amount of 18.9 g (85% yield). When recrystallized from ethanol, it melted at 230° C (decomp.), gave an $R_f$ value of 0.60, and was identified by elementary analysis:

Calculated for $C_{14}H_{14}I_4O_8$: 20.56%, C; 62.07%, I. Found: 20.78%, C; 61.97%, I.

EXAMPLE 3

21.4 g Di-sodium tetra-iodoterephthalate, 0.5 g sodium iodide, and 10 g 2-chloropropanol were heated with stirring in 150 ml dimethylformamide at 100° C for 10 hours. The solvent was distilled off, and the residue was suspended in water and purified as described in Example 1. 14.15 g Bis-1-hydroxy-2-propyl ester of tetra-iodoterephthalic acid (60% yield) was recovered. It melted and decomposed at about 225° C.

EXAMPLE 4

When an equal weight of 3-chloropropanol was substituted for 2-chloropropanol in the procedure of Example 3, 15.3 g bis-3-hydroxypropyl ester of tetra-iodoterephthalic acid (65% yield) was obtained and melted at approximately 205° – 206° C with decomposition. Thin layer chromatography with butyl acetate/glacial acetic acid/water 5:1:1 gave an $R_f$ value of 0.66. The ester was identified by elementary analysis:

Calculated for $C_{14}H_{14}I_4O_6$: 64.59% I. Found: 65.12%, I.

EXAMPLE 5

35.7 g Di-sodium tetra-iodoterephthalate (0.05 mole) and 0.5 g sodium iodide were stirred in 50 ml 2-chloro-1,3-propanediol for 60 hours at 100° C. The unreacted 2-chloro-1,3-propanol was distilled off, and the residue was washed sequentially with water, sodium carbonate solution, and again water. The washed and dried residue weighed 29 g (71% yield) and consisted essentially of bis-1,3-dihydroxy-2-propyl ester of tetra-iodoterephthalic acid. When recrystallized from 50% ethanol, its melting point was above 250° C. A thin-layer chromatogram with chloroform/methanol/glacial acetic acid 10:5:1 gave an $R_f$ value of 0.88. Upon partial elementary analysis, an iodine content of 61.83% was found as compared to the value of 62.07% calculated for $C_{14}H_{14}I_4O_8$.

EXAMPLE 6

21.4 g Tetra-iodoterephthalic acid (0.03 mole) and 2 g anhydrous sodium acetate in 150 ml dimethylformamide were mixed with 20 g propylene oxide, and the mixture was stored in a sealed vessel for about 4 hours at 80° – 90° C. It was then evaporated to dryness, and the residue was taken up in water and further washed with sodium bicarbonate solution and water. The recovered bis-2-hydroxypropyl ester of tetra-iodoterephthalic acid weighed 14.9 g (63% yield) and melted at approximately 220° C (decomp.) after recrystallization from ethanol.

EXAMPLE 7

14.12 g Tetra-iodoterephthaloyl dichloride (0.020 mole) in 150 ml dimethylformamide was added dropwise with vigorous agitation to a solution of 8 g 2,2-dimethyl-1,3-dioxolane-4-methanol (0.06 mole) and 8 ml pyridine in 100 ml dimethylformamide. The completed mixture was stirred a few hours longer and then evaporated. The residue was digested with water for purification, dissolved in dimethylformamide, and mixed with approximately 1–2 ml of diethyl ether saturated with HCl. The solution then was evaporated to dryness in a vacuum, and the residue was washed sequentially with water, dilute sodium bicarbonate solution, and again with water.

The bis-2,3-dihydroxypropyl ester of tetra-iodoterephthalic acid was obtained in an amount of 9 g (55% yield) and melted at 230° C.

EXAMPLE 8

14. g Tetra-iodoterephthaloyl dichloride (0.02 mole) was suspended in 40 ml diethylene glycol, and the suspension was mixed with 3.95 g pyridine (0.05 mole) and stirred for three hours at 120° C. When thereafter cooled to room temperature, the reaction mixture was stirred into 250 ml 0.3% aqueous hydrochloric acid. The precipitated bis-2-(2'-hydroxyethoxy)-ethyl ester of tetra-iodoterephthalic acid was washed with water and sodium bicarbonate solution and recovered in an amount of 15.5 g (91.5% yield). When recrystallized from 95% ethanol, it melted at 166° C and gave an $R_f$ value of 0.5 in a thin-layer chromatogram with butyl acetate/glacial acetic acid/water 5:1:1. It was found to contain 59.84% iodine as compared to 60.01% calculated for $C_{16}H_{18}I_4O_8$.

The same compound was also obtained from 19.4 g di-sodium tetra-iodoterephthalate, 0.5 g sodium iodide, and 30 ml diethylene glycol monochlorohydrin by a procedure analogous to that of Example 1.

EXAMPLE 9

When an equal volume of 1,4-butanediol was substituted for the diethylene glycol in the procedure of Example 8, the bis-4-hydroxybutyl ester of tetra-iodoterephthalic acid was obtained in an amount of 14.9 g (91.5% yield). When recrystallized from aqueous dioxan, it melted at about 140° C and gave an $R_f$ value of 0.67 under the conditions of Example 8. 62.04% Iodine were found 63.37% calculated for $C_{16}H_{18}I_4O_6$.

EXAMPLE 10

22.4 g Tetra-iodeterphthalic acid (0.033 mole), 200 ml ethylene glycol, and 8 ml concentrated sulfuric acid were stirred at 100° C for about five hours. The reaction mixture was cooled to ambient temperature and stirred into one liter water. When the aqueous mixture was neutralized with 5% aqueous ammonia, the bis-2-hydroxyethyl ester of tetra-iodoterephthalic acid was prepared. It was washed with sodium bicarbonate solution and water and recovered. It weighed 16.3 g (65% yield) and melted at 260° C (decomp.).

Among the compounds of the invention, the bis-2-hydroxyethyl, bis-2-hydroxypropyl, and bis-2,3-dihydroxypropyl esters of tetra-iodoterephthalic acid combine low toxicity, rapid excretion, opacity to X-rays, and other advantages features in a most desirable manner and the presently preferred. However, the corresponding 1-hydroxymethyl-2-hydroxyethyl, 1-methyl-2-hydroxyethyl, 3-hydroxypropyl, 4-hydroxybutyl, and 2-(2'-hydroxyethoxy)-ethyl esters are almost equally superior to the known lower-alkyl esters of tetra-iodoterephthalic acid, and the other compounds encompassed by the above formula share at least some of these advantages over the chemically closest known compounds.

While the invention has been described with particular reference to specific embodiments, it is to be understood that it is not limited thereto, but is to be construed broadly and restricted solely by the scope of the appended claims.

What is claimed is:

1. A compound of the formula

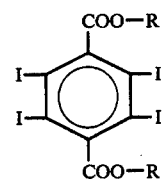

wherein R is 2-hydroxyethyl, 2,3-dihydroxypropyl, 1-hydroxy-2-propyl, 3-hydroxypropyl, 1,3-dihydroxy-2-propyl, 2-hydroxypropyl, 4-hydroxybutyl, or 2-(2'-hydroxyethoxy)-ethyl.

2. A compound as set forth in claim 1, wherein R is $CH_2$—CHOH—R', R' beng H, $CH_3$, or $CH_2OH$.

3. A compound as set forth in claim 2, wherein R' is H.

4. A compound as set forth in claim 2, wherein R' is $CH_3$.

5. A compound as set forth in claim 2, wherein R' is $CH_2OH$.

6. A compound as set forth in claim 1, wherein R is 1,3-dihydroxy-2-propyl.

7. A compound as set forth in claim 1, wherein R is 1-hydroxy-2-propyl.

8. A compound as set forth in claim 1, wherein R is 3-hydroxypropyl

9. A compound as set forth in claim 1, wherein R is 4-hydroxybutyl.

10. A compound as setforth in claim 1, wherein R is 2-(2'-hydroxyethoxy)-ethyl.

11. A compound as set forth in claim 1 having a radioactive iodine atom.

* * * * *